(12) United States Patent
Herrmann et al.

(10) Patent No.: US 7,793,664 B2
(45) Date of Patent: Sep. 14, 2010

(54) APPARATUS AND METHOD FOR DETECTION AND SEGREGATION OF FAULTY CIGARETTES

(75) Inventors: Rainer Herrmann, Hamburg (DE); Udo Schlemm, Hamburg (DE); Hendrik Richter, Hamburg (DE)

(73) Assignee: TEWS Elektronik Dipl.-Ing. Manfred Tews, Hamburg (DE)

( * ) Notice: Subject to any disclaimer, the term of this patent is extended or adjusted under 35 U.S.C. 154(b) by 987 days.

(21) Appl. No.: 11/477,749

(22) Filed: Jun. 28, 2006

(65) Prior Publication Data

US 2007/0000503 A1   Jan. 4, 2007

(30) Foreign Application Priority Data

Jul. 1, 2005   (DE)   .................. 20 2005 010 375 U (51) Int. Cl.
*A24C 5/32*   (2006.01)
*A24C 5/34*   (2006.01)

(52) U.S. Cl. ..................... 131/280; 131/908; 131/905; 131/108; 324/640; 324/634; 324/636; 73/29.05

(58) Field of Classification Search ................ None
See application file for complete search history.

(56) References Cited

U.S. PATENT DOCUMENTS 3,729,636 A   4/1973   Merker .................. 250/223 R
4,376,484 A   3/1983   Seragnoli ................... 209/535
4,592,470 A   6/1986   Mattei .......................... 209/535
4,742,668 A   5/1988   Ecabert ........................ 53/494
5,977,780 A *  11/1999   Herrmann .................... 324/640
2003/0178036 A1*  9/2003   Demmer et al. ............. 131/280

FOREIGN PATENT DOCUMENTS

| | | |
|---|---|---|
| CA | 1048809 | 2/1979 |
| DE | 2 236 218 A | 3/1973 |
| DE | 2 625 001 A | 12/1976 |
| DE | 3 439 945 | 6/1985 |
| DE | 4004 119 A1 | 8/1991 |
| EP | 0889 321 A1 | 1/1999 |
| EP | 1371979 A1 | 12/2003 |

* cited by examiner

*Primary Examiner*—Philip C Tucker
*Assistant Examiner*—Phu H Nguyen
(74) *Attorney, Agent, or Firm*—Alix, Yale & Ristas, LLP (57) ABSTRACT

Apparatus and method for detection and segregation of faulty cigarettes in a production/packaging installation for cigarettes having an apparatus by means of which faulty cigarettes are segregated from the conveyed sequence of cigarettes, wherein the apparatus and method use a generator and evaluation circuits for radio-frequency electromagnetic fields and use a sensor past whose end surface the ends of the cigarettes are passed and which applies the radio-frequency electromagnetic fields to the end surface of the sensor, whose size corresponds approximately to the size of the end surface of the cigarettes, with the changes in the electromagnetic fields as a cigarette passes being evaluated.

21 Claims, 10 Drawing Sheets

APPARATUS AND METHOD FOR DETECTION AND SEGREGATION OF FAULTY CIGARETTES

BACKGROUND OF THE INVENTION

The invention relates to an apparatus and a method for detection and segregation of faulty cigarettes in a production/packaging installation for cigarettes having an apparatus by means of which faulty cigarettes are segregated from the conveyed sequence of cigarettes.

In cigarette production, care is generally taken to ensure that there is an increased tobacco density at the burning end of the cigarette, in order to prevent tobacco from falling out as a result of the quite varied movements of the cigarette when being transported between the cigarette machine and the packing machine, or else subsequently within the packaging. Nevertheless, tobacco falls out of the end of the cigarette repeatedly when, for example, the tobacco becomes too dry. The presence of loose tobacco or of cavities at the cigarette ends leads to a poorer quality product. Efforts have therefore been made for many years in the process of cigarette manufacture in order to prevent the occurrence of such faulty cigarettes, in particular by means of experiments to detect such defects and to reject faulty cartons or cigarettes.

Until now, electromechanical methods with a stamp or a large number of stamps, or optical or infrared measurement methods, have primarily been used as the methods for detection of faulty cigarette ends.

In the case of electromechanical methods, which have been known for decades (see for example GD application U.S. Pat. No. 4,376,484 A dated Mar. 15, 1983 or DE 3 439 945 dated Jun. 20, 1985), a stamp or a group of stamps is moved towards the cigarette ends, and the penetration depth is recorded. For an optimum measurement result, the cigarette must for this purpose be stopped exactly at the position of the stamp, and any slight overlap of the stamp with the paper area of the cigarette would corrupt the measurement result. At the speeds which occur nowadays in the packing machine, this would mean a measurement device that is highly sensitive to mechanical destruction in the machine, with a negative influence on the possible transport and machine speeds. Particularly in the input area, where rapid and precise positioning for individual detection and individual ejection is extremely difficult, this measurement method has been found to be too inaccurate. Furthermore, the product is adversely affected by the mechanical contact with the stamp. This method can only inaccurately detect certain critical shapes of a point in which there is no tobacco, but which occur frequently, such as that of a cone in which there is no tobacco at the edge of the cigarette but tobacco is still present in the center.

In order to overcome these shortcomings, non-contacting methods have been developed repeatedly in the last 30 years, which are based on the back-scattering of light in the visible band or in the infrared band (see, for example, BAT, DE 2 236 218 A dated Mar. 29, 1973 or AMF Inc., DE 2 625 001 A dated Dec. 16, 1976 or Burrus S A, U.S. Pat. No. 4,742,668 A dated May 10, 1988). These methods have the advantage that the cigarettes need not be stopped as their end surfaces move transversely through the measurement zone of the sensors. This allows higher production rates. On the other hand, the measurement effect that is used here of reflection of the light on the cross-sectional surface of the cigarette is a pure surface effect. In consequence, even a single tobacco fiber which conceals a tobacco hole can make it impossible to detect this defect. In this case as well, conical defects which often occur in the center of the cross section but contain a small amount of tobacco at the paper edge cannot be identified. In addition, color fluctuations in the tobacco blend or fluctuations in the moisture in the tobacco result in a change in the reflection behavior, so that there is a relatively high level of measurement uncertainty in the detection of defective cigarettes.

The object of the invention is to provide a method by means of which a noncontacting measurement can be carried out which records not only the surface but also areas located underneath it in the cigarettes.

SUMMARY OF THE INVENTION

The solution according to the invention consists in that a generator and evaluation circuits are provided for radio-frequency electromagnetic fields, and a sensor past whose end surface the ends of the cigarettes are passed and which applies the radio frequency electromagnetic fields to the end surface of the sensor, whose size corresponds approximately to the size of the end surface of the cigarettes, with the changes in the electromagnetic fields as a cigarette passes being evaluated.

The radio-frequency electromagnetic fields penetrate into the cigarette at the end of the cigarette (or at both ends when sensors are provided on both sides). The radio-frequency electromagnetic fields are influenced not only by faults on the surface but also by faults located underneath it in the end area of the cigarette. In contrast to, for example, the mechanical measurement methods, faults are also identified in which there is no tobacco at the edge of the cigarette, but tobacco is still present in the center. In contrast to optical methods, the arrangement according to the invention also has the advantage that it is not influenced by color fluctuations.

In one advantageous embodiment, two electrically isolated conductor structures which are arranged on the end surface of the sensor are used as the sensor; and have the characteristics of a capacitor (for example two capacitor plates). The capacitance of the capacitor varies as a function of the dielectric constants of the tobacco or of the filter at the end of the cigarette. In the case of correct cigarettes, the capacitance will in this case assume values which are within a specific range. If the capacitance for one cigarette is outside this range, then this cigarette is faulty and can be rejected.

The capacitance and the capacitance changes may in particular be measured by means of an LC circuit, with the two plates forming the capacitor C.

One particularly advantageous embodiment is distinguished in that the sensors are microwave resonators which are open on their end face pointing towards the cigarette and have an electrically conductive pin on their axis, which pin is fitted to the closed end surface of the microwave resonator and has a length which corresponds approximately to one quarter or three quarters of the microwave wavelength. In this case, the cavity in the microwave resonator and/or the pin are/is advantageously cylindrically symmetrical.

The microwave resonator method which has been developed and described by the applicant according to the patent "Verfahren zur Messung der Feuchte eines Messgutes mit Hilfe van Mikrowellen und Vorrichtung zur Durchführung des Verfahrens" [Method for measurement of the moisture in a measured goods with the aid of microwaves and apparatus for carrying out the method], (DE 4004 119 C2) makes it possible to measure two independent parameters, which are determined from the shift in the resonant frequency and the broadening of the resonance curve. These two measured parameters were first of all used to carry out a mass-independent moisture measurement (DE 4004119 C2). A profile measurement of the mass and of the moisture in objects has also already been documented (TEWS Patent, 'Feuchte- und Dichtesensor' [Moisture and density sensor] EP 0889 321 A1). Subsequently, a moisture-independent mass measurement was also described, using resonators with a homogeneous measurement field (for example TEWS patent application "Mikrowellenvorrichtung zur Qualitätsprüfung strangförmiger Materialien" [Microwave apparatus for quality testing of materials in the form of strands] EP 1371979 A1).

In order to use microwave resonators to detect faulty cigarettes, it is necessary to measure the area-related mass with the aid of a stray field sensor. A density measurement is not sufficient for this purpose since the density is often distributed very inhomogeneously in the cigarette tip, particularly when defects are present: For a volume-related mass measurement, it is necessary for the strength of the measurement field to be homogeneous in the area in which the measured goods are placed. In order to measure an area-related mass, it is necessary for the measurement field to be homogeneous, at least over the diameter of a cigarette, in two dimensions at right angles to the cigarette axis. This is the only way in which tobacco defects can be detected independently of their position and of the field distribution with the same strength. Stray field resonators which have been known until now have a field which is inhomogeneous in all spatial directions, however. According to the invention, it was therefore necessary to develop new stray field sensors for detection of defects in cigarette ends.

In addition to the high homogeneity of the sensor stray field in two dimensions in the area of the cigarette head at right angles to the cigarette axis in order to measure the area-related mass of the cigarette end, a stray field sensor must have the 5 following characteristics:

1) In order to allow the area-related mass of individual cigarettes to be measured, a resonator must have sufficiently good position resolution, that is to say the measurement field must fall away sharply outside the area of the cigarette head, in order to avoid the measurement being influenced by adjacent cigarettes. On the other hand, the stray field must extend beyond the cigarette head with the homogeneity referred to above.
2) A stray field sensor must be sufficiently sensitive, that is to say it must be possible to detect even minor defects as being significant by means of the sensor.
3) In order to allow an error-free measurement to be carried out of the two parameters of the microwave resonator method of TEWS Electronics, it is necessary for no microwave field energy from the resonator stray field to be lost by emission into space.
4) In order to record significantly more tobacco in the cigarette tip than is possible with a pure surface measurement the stray field must penetrate for a few millimeters into the depth of the cigarette end, without microwave energy being radiated out.
5) The resonator geometry must include space for the input and output antennas for the microwave signal, so that sufficiently strong coupling of the sensor is ensured.

A stray field resonator with coaxial geometry is generally suitable for achieving the measurement object. The resonator comprises a cylindrical cavity, whose opening corresponds approximately to the diameter of a cigarette. A cylindrical pin is located in this cavity, with a length which corresponds approximately to one quarter or three quarters of the wavelength of the microwave field. In consequence, a standing wave at about one quarter or three quarters of the wavelength is formed between the wall of the cavity and the pin. An axially symmetrical stray field is produced at the opening of the resonator, and falls away exponentially in the axial direction outside the resonator.

In the case of a coaxial resonator, the measurement frequency is governed mainly by the length of the pin or of the cavity, and is intended to be in the frequency range from 1 to 10 GHz, in particular from 2 to 3 GHz. The radius of the resonator opening is defined roughly by the radius of a cigarette.

One major advantage of measurement using microwaves is that the mass and material density can be determined independently of the material moisture. This lack of dependence on the material moisture is also important because, during the cigarette production process, it is often sometimes possible for the cigarettes to remain for different time periods, and to be able to dry out severely, on their way between the cigarette machine and the packing machine, via the circuitous route through a buffer or when being transported by means of inclines. It is therefore not rare for the tobacco moisture in the cigarette, particularly at the cigarette end, to fluctuate between 8% and 14% moisture. Furthermore, the microwave method offers the advantage that, in parallel with the measurement signal of the mass at the end of the cigarette, it indicates the tobacco moisture, that is to say can also at the same time detect a possible cause for an increased head failure, specifically that the cigarette may have dried out excessively. Measurement with microwaves also has the advantage that it is independent of color fluctuations of the tobacco, and of the tobacco mixture itself.

The apparatus according to the invention and the method make it possible to identify faulty cigarettes, and to reject them more easily and more reliably than the previously used methods. In this case, on the one hand, it is possible to use the microwave method at measurement positions where entire groups of cigarettes are formed, and thus to eject entire groups when a faulty cigarette is present. On the other hand, this method can also be used for detection of individual cigarettes, and to eject them individually.

In the case of filter cigarettes, a fault is also present when no filter element has been fitted during production. This can additionally be detected by carrying out measurements at both ends of the cigarette. In the input to a packing machine, the cigarettes are first of all moved in a broad funnel parallel to one another but at right angles to their longitudinal direction and, shortly before reaching the packing machine, are guided in individual rows, with the number of rows corresponding to the number of cigarettes in a package. If a sensor for detection of faulty cigarettes, or two sensors for measurement at both ends of the cigarette, is or are fitted in each of these rows, individual faulty cigarettes can be identified and reliably ejected. This has been known as an idea for a long time, although it has not been possible to implement it in practice because of the high error rate with previous sensors. However, this has become possible by means of microwave resonators.

One advantageous embodiment of a coaxial resonator for identification of defective cigarettes is distinguished in that the pin has a length which is approximately 1 to 20% less than the axial extent of the microwave resonator. In particular, it is advantageous for the pin to have a length which is less by approximately 2 to 8% than the axial extent of the microwave resonator.

In this case, the diameter of the pin is advantageously approximately 30 to 90% of the internal diameter of the microwave resonator. It is particularly advantageous for the diameter of the pin to be approximately 65 to 85% of the internal diameter of the microwave resonator.

Another advantageous embodiment provides for the microwave resonator to taper at its open end and then to widen outwards in a truncated-conical shape, and for the pin at the same time to taper in a truncated-conical shape at this end of the microwave resonator.

In this case, the diameter of the pin is advantageously approximately 30 to 70% of the internal diameter of the microwave resonator.

The opening in the microwave resonator is advantageously closed by a dielectric in order to prevent the penetration of impurities into the microwave resonator. It has been found to be particularly expedient for the opening in the microwave resonator to be closed by a ceramic disk. This is particularly wear-resistant, and this is advantageous because of the large number of cigarettes that are produced and moved past the sensor during mass production.

If the microwave resonators are provided at a point at which the cigarettes are arranged in groups to form a plurality of layers, with one microwave resonator (or two microwave resonators at both ends of the cigarettes) being provided for each layer, this has the advantage that only a relatively small number of microwave resonators are required. The disadvantage is that, in this case, the entire group must be ejected on detection of one faulty cigarette.

Another advantageous embodiment therefore provides for the microwave resonators to be provided at a point past which the cigarettes are passed individually. A greater number of microwave resonators and corresponding evaluation circuits are then required. However, only the faulty cigarette need be ejected in each case, which means less waste.

BRIEF DESCRIPTION OF THE DRAWINGS

The invention will be described in the following text using advantageous embodiments and with reference to the attached drawings, in which.

DETAILED DESCRIPTION OF THE PREFERRED EMBODIMENTS

Figure 1:
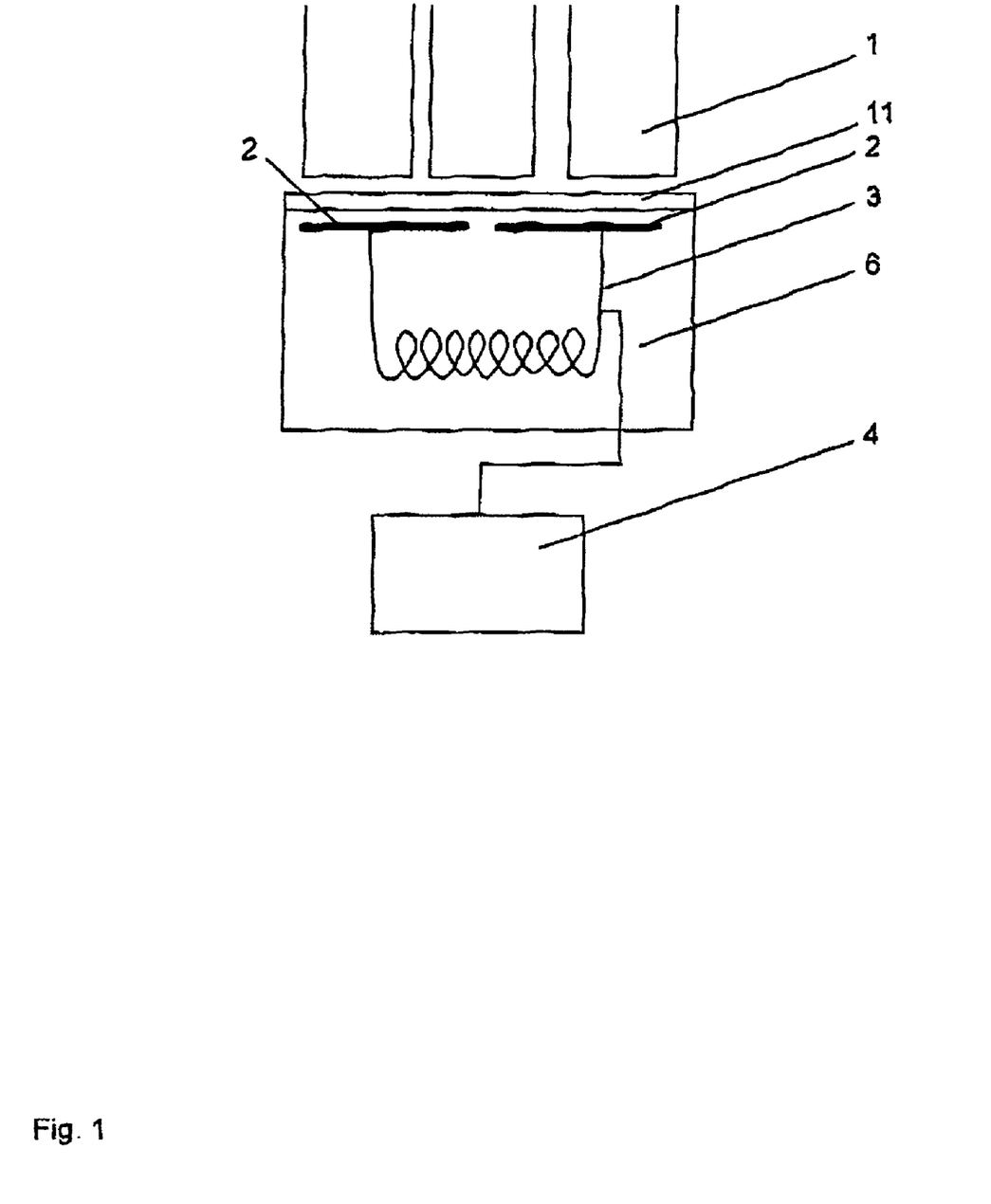
FIG. 1 shows a schematic illustration of a first embodiment of the invention.
Figure 2:
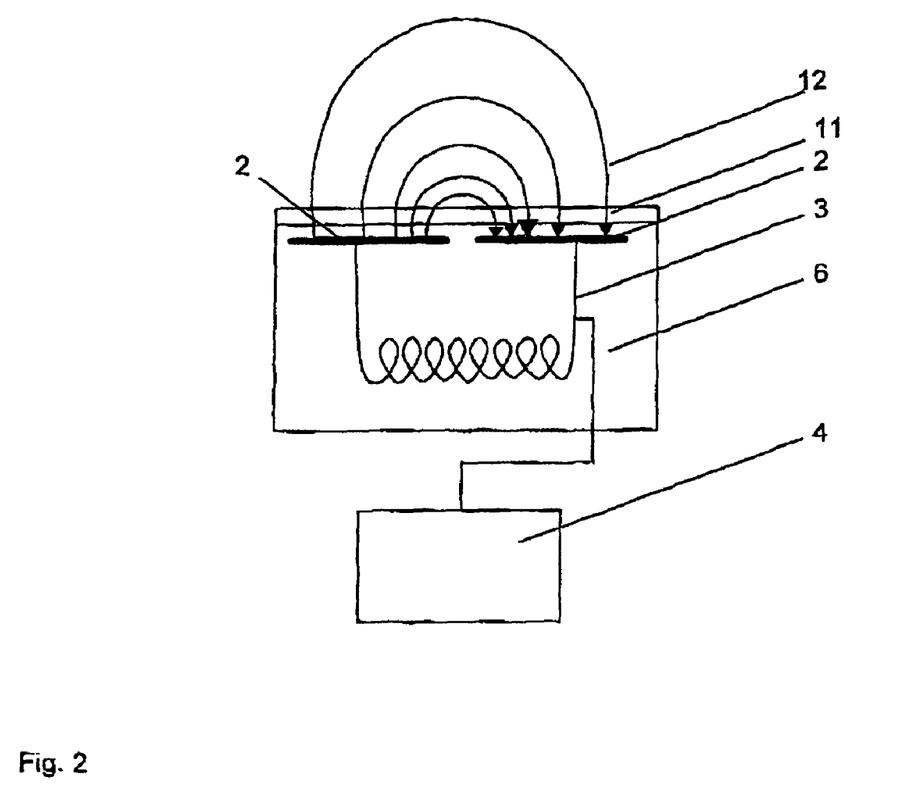
FIG. 2 shows a detailed view of the sensor shown in FIG. 1, with the profile of the electrical field lines.

FIG. 1 shows, schematically, a first apparatus according to the invention. A cigarette 1 is moved past two electrically isolated conductor structures 2 which form a capacitor C. The conductor structures are connected to one another by means of an inductance L with the reference number 3. Radio frequency is applied to the resonant circuit LC by means of a circuit 4. This circuit 4 is then also used to detect any change in the resonance response caused by the cigarette 1 moving past. As can be seen from FIG. 2, the electrical field lines 5 run from one conductor structure 2 to the other, so that they penetrate into the end of the cigarette 1. Faults in the end area of the cigarette 1 can be found in this way.

Figure 3:
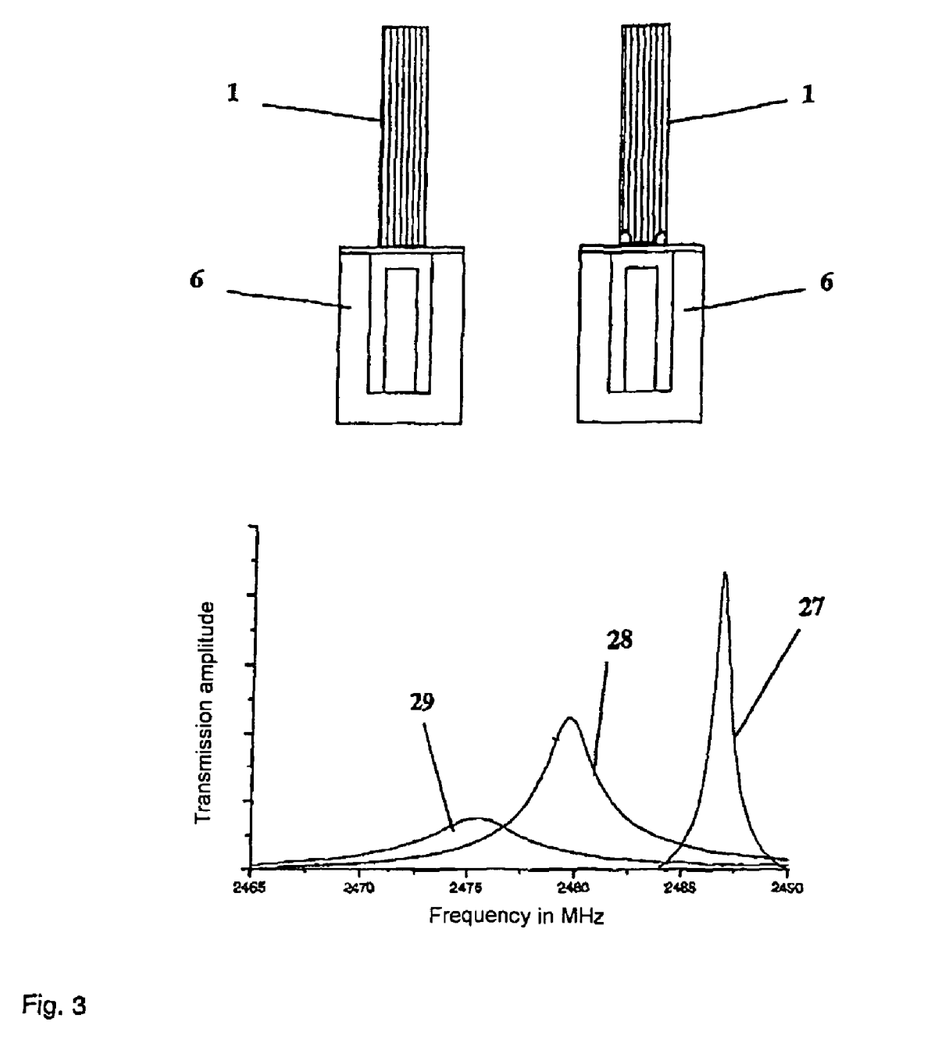
FIG. 3 shows, at the top on the left, another embodiment of the sensor with an intact cigarette, at the top on the right the sensor with a faulty cigarette, and at the bottom the microwave spectra for different cases.

FIG. 3 shows a different, particularly advantageous embodiment of the sensor according to the invention in the form of a microwave resonator 6. A good cigarette 1 is arranged at the top on the left in front of the microwave resonator 6 in the illustration, while a faulty cigarette 1 is arranged in front of the microwave resonator 6 at the top on the right in the illustration. The resonant frequencies are illustrated for various situations in the lower part of FIG. 1. The resonance curve of the empty microwave resonator 6 is shown at 27. The resonance curve of the microwave resonator 6, in front of which a good cigarette 1 is located, is shown at 29. The resonance curve of the microwave resonator 6 in front of which a faulty cigarette 1 is located is shown at 28.

Figure 4:
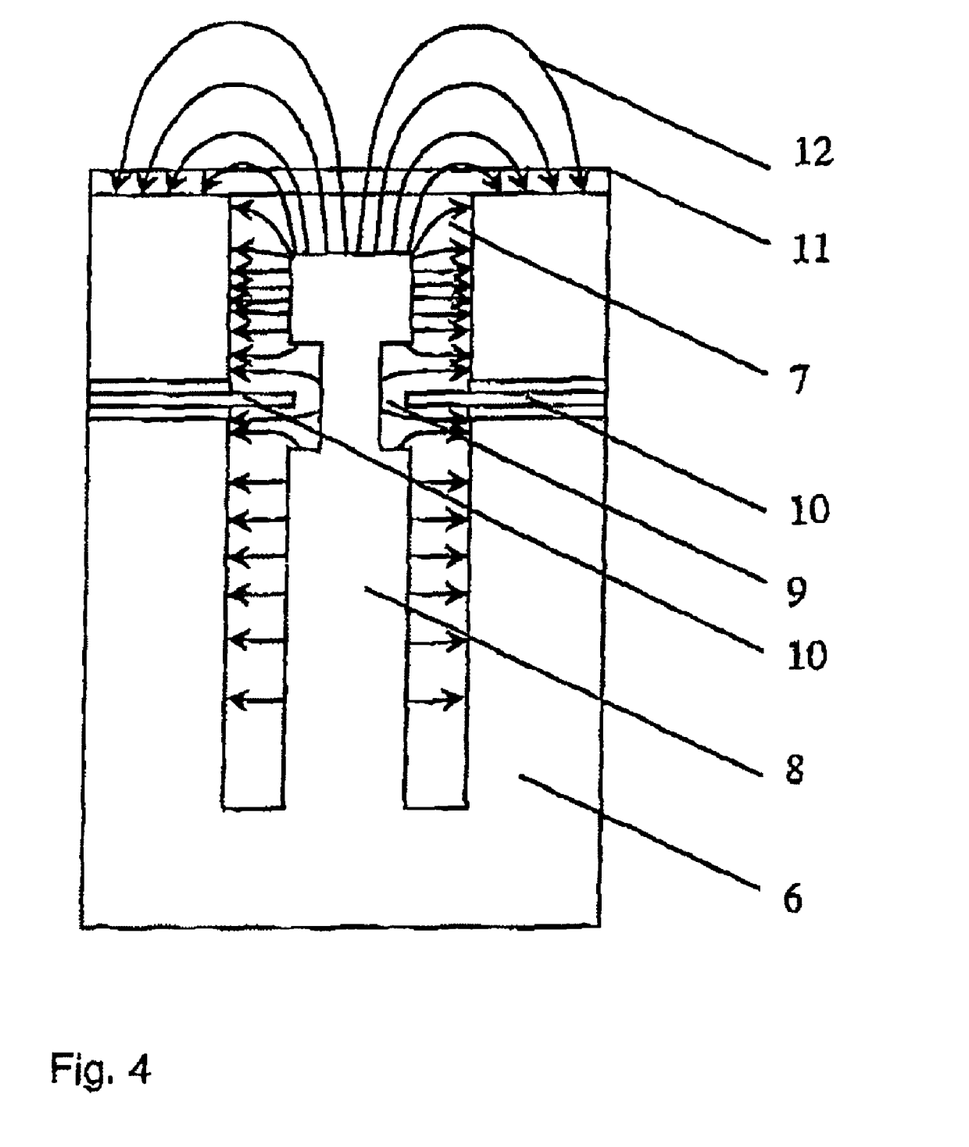
FIG. 4 shows a detailed view of the sensor from FIG. 3.
Figure 6:
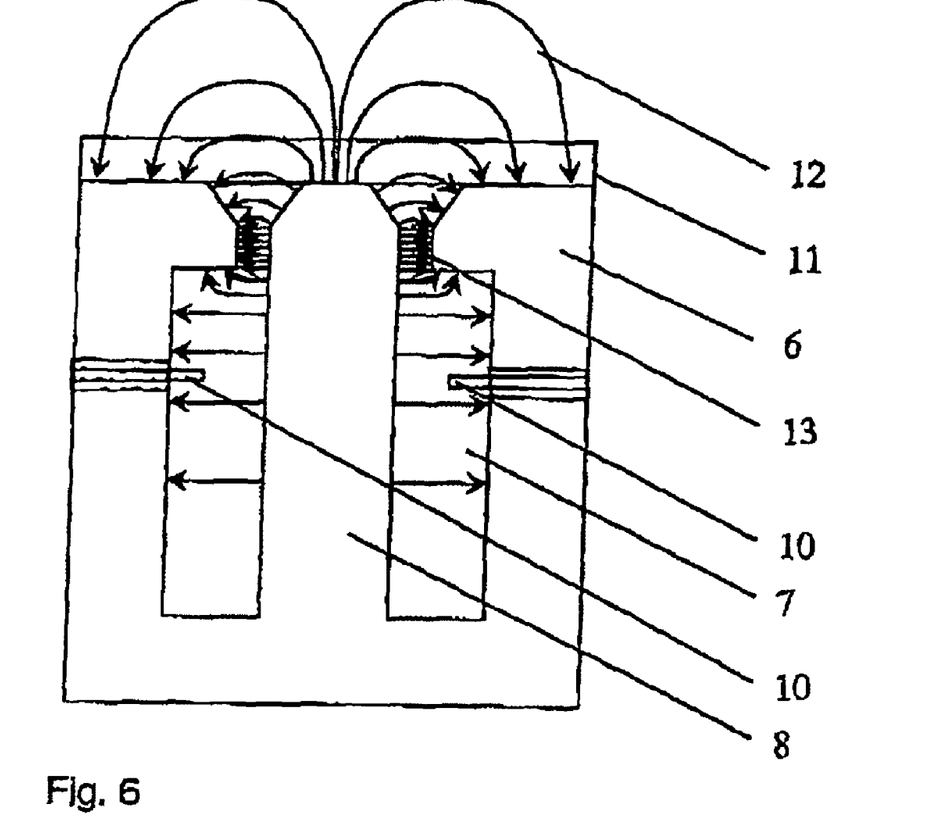
FIG. 6 shows a further embodiment of the sensor according to the invention.

Examples of the microwave resonator 6 shown in FIG. 3 are illustrated in more detail in FIG. 4 and FIG. 6. The microwave resonator 6 has a cylindrical resonator cavity 7, in which a resonator pin 8 is arranged on the axis of the resonator cavity 7, is attached to the base of the resonator cavity 7, and ends slightly below the upper opening of the resonator cavity 7. The resonator pin 8 is provided with a constriction 9 in order to create space there for antennas 10, which are used for inputting and outputting the microwaves. The corresponding electronic circuits for production and evaluation of the microwaves are not illustrated in the figure. The microwave resonator 6 is covered by a ceramic disk 11. The electrical field lines are illustrated at 12 and, as can be seen, are concentrated strongly on the end face of the microwave resonator 6, which is covered by the ceramic disk.

Shortening of the pin 8 with respect to the cavity 7 results firstly in the field concentrations in the area of the edges and the area of low field strength in the pin center being distanced from the measured goods, and in a homogeneous measurement field, in the form of a plateau, being made available in the area of the cigarette head. After shortening of the pin 8 with respect to the cavity 7 it is possible to choose the pin radius such that the measurement field has a constant profile in the area of the cigarette head, and falls away exponentially in the radial direction outside the cigarette head. This means, for the first time, that it is possible to measure the area-related mass independently of the local position of an inhomogeneous mass distribution.

The shortening of the pin 8 with respect to the cavity 7 secondly makes it possible to prevent the emission of microwave energy, since the microwave field energy is more strongly linked to the resonator.

Shortening of the pin 8 with respect to the cavity 7 thirdly makes it possible to increase the penetration depth of the stray field into the cigarette head, since field components which fall away more than exponentially in the area of the edges are at a distance from the cigarette head, which effectively leads to an enlargement of the penetration depth into the cigarette ends.

The sensitivity of the sensor is reduced by shortening the pin 8 with respect to the cavity 7 and by enlarging the pin radius. Shortening the pin with respect to the cavity and suitable choice of the pin radius make it possible to produce a stray field sensor whose lateral measurement field is highly homogeneous, with a sensitivity which is still adequate.

In the exemplary embodiment shown in FIG. 4, the compliance according to the invention with the condition 5 is achieved by providing the pin 8 with a circumferential constriction 9, which creates space for the antennas 10 for capacitive inputting and outputting of the microwave signal. The antennas are mounted at the side.

Figure 5:
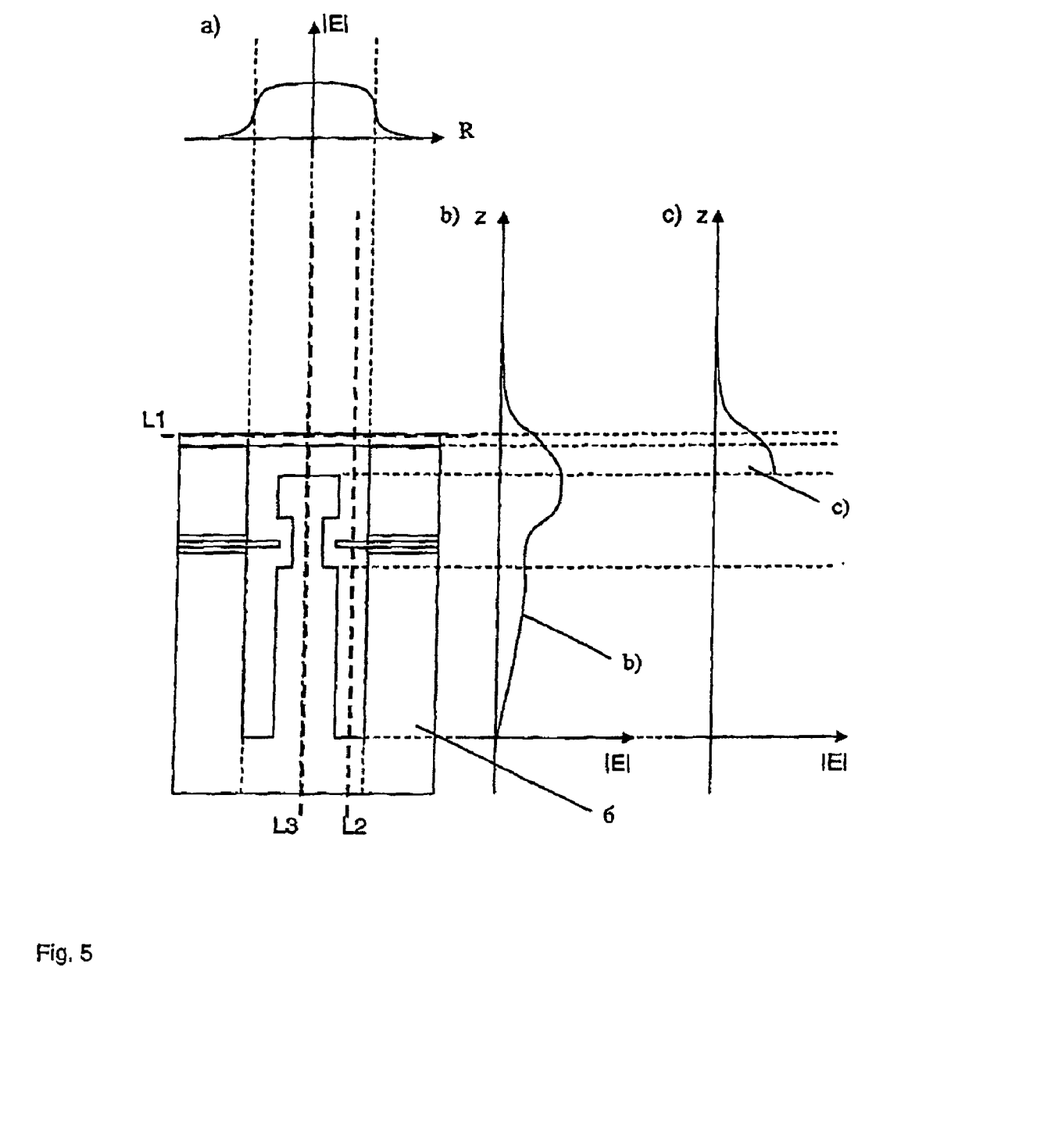
FIG. 5 shows a further illustration of the sensor from FIG. 3, showing the field strengths.

FIG. 5 shows the field strength distribution, that is to say the intensity of the electrical field of the microwave resonator 6 in FIG. 4, to be precise at a) the field strength distribution on the line L1, at b) the field strength distribution on the line L2 and at c) the field strength distribution on the line L3.

The microwave resonator 6 shown in FIG. 6 has a similar design to that shown in FIG. 4. The differences are as follows: the resonator cavity 7 is broader than that in FIG. 4, and there is no need for any constriction 9 in order to create space for the antennas 10. However, the resonator cavity 7 tapers in the vicinity of its open end and thus creates a field concentration zone 13. The microwave resonator 6 widens in a truncated-conical shape at the open end, while the pin 8 tapers in a truncated-conical shape. The electrical field lines are once again shown at 12.

The compliance according to the invention with the conditions described above is achieved in the exemplary embodiment shown in FIG. 6 firstly by the gap between the cavity wall and the pin tapering at the opening (field concentration zone 13), and secondly by the pin 8 having a conically running taper at its tip, and by the opening of the cavity being widened in a funnel shape.

The provision of the field concentration zone 13 and of the zone which widens in a funnel shape firstly make it possible to avoid the disturbing effect of field concentrations in the area of the edges in the end area of the cigarette and to make available a measurement field, which is in the form of a plateau, in the area of the cigarette head. These measures mean that it is possible to choose the pin radius such that the measurement field has a constant profile in the area of the cigarette head, and falls away exponentially in the radial direction outside the cigarette head.

The provision of the field concentration zone 13 secondly makes it possible to prevent the emission of microwave energy, since the field remains strongly linked to the resonator within the field concentration zone, and is thus not emitted.

The creation of a zone which widens in a funnel shape thirdly makes it possible to increase the penetration depth of the stray field into the cigarette head, since field components which fall away more than exponentially in the area of the edges are avoided.

The provision of the field concentration zone 13 fourthly makes it possible to greatly increase the sensitivity of the sensor, since the ratio of the field energy in the measurement zone above the zone which widens in a funnel shape is sufficiently large relative to the field energy in the field concentration zone.

There is sufficient space for the antennas 10 to be arranged underneath the field concentration zone.

Figure 7:
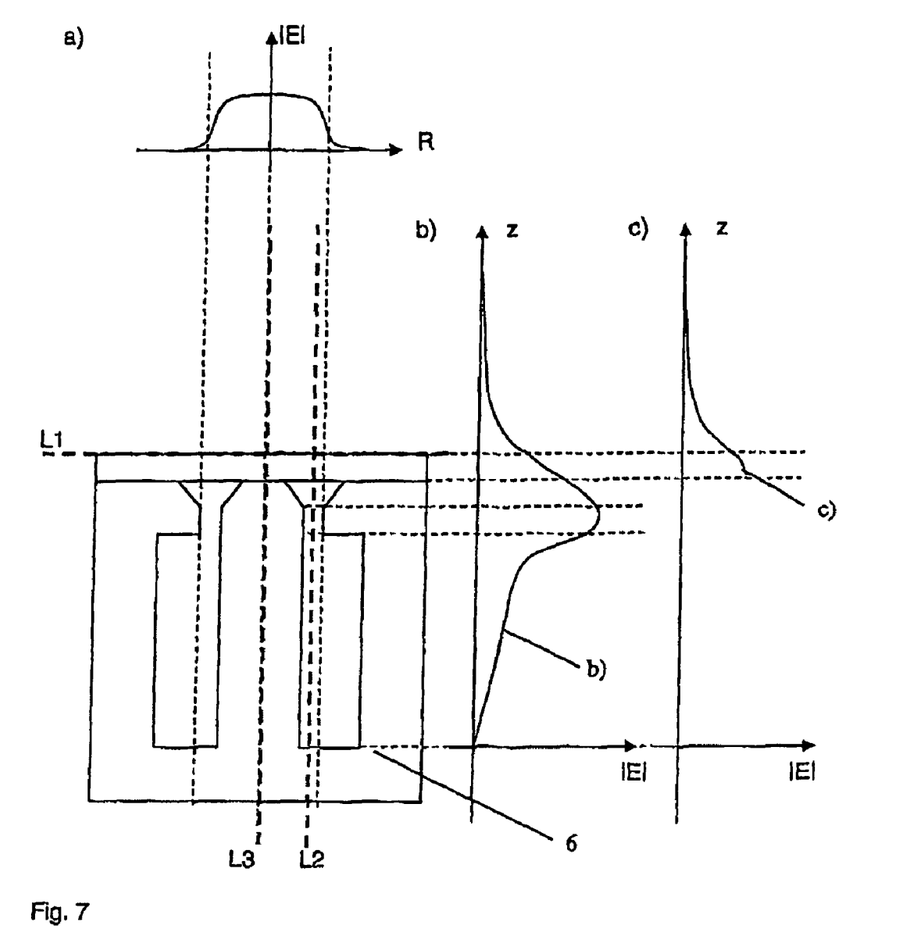
FIG. 7 shows an illustration of the sensor from FIG. 6, showing the field strengths.

FIG. 7 shows the field strength distribution, that is to say the intensity of the electrical field of the microwave resonator 6 from FIG. 6, to be precise at a) the field strength distribution op the line L1, at b) the field strength distribution on the line L2, and at c) the field strength distribution on the line L3.

In the case of the microwave resonator method, two resonance parameters are measured for each measurement. The first of the measured variables is the shift in the resonant frequency A in Hz which occurs as a result of the introduction of the head of a cigarette into the measurement field (see FIG. 3)

$$A = f_0 - f_m \quad (1)$$

where $f_0$: resonant frequency of the empty resonator in Hz $f_m$: resonant frequency with a cigarette end in the measurement field of the resonator Hz The second measured variable is the increase in the 3 dB width of the resonance B in Hz:

$$B = w_m - w_0 \quad (2)$$

where $w_0$: 3 dB width of the resonance of the empty resonator in Hz $w_m$: 3 dB width of the resonance with a cigarette end in the measurement field of the resonator in Hz Since the two parameters A and B are mass-dependent in the same way, the quotient of the two variables is mass-independent. The mass-independent microwave moisture value $\Phi$ is obtained as follows from this quotient:

$$\Phi = \arctan(B/A) \quad (3)$$

The area-related mass $m_f$ must be determined taking into account the moisture in the cigarettes, since a varying moisture content resulting from the high dielectric constant of the water would otherwise render the area-related mass measurement impossible. One suitable relationship for determination of the area-related mass with moisture compensation is as follows:

$$m_f = a_1 \cdot A + a_2 \cdot A \cdot \Phi + a_3 \quad (4)$$

where $a_i$: calibration coefficient

The area-related mass $m_f$ with moisture compensation is the measured value which is required in order to decide whether a cigarette defect is present. The expression (4) offers major advantages:

1. The value for the area-related mass $m_f$ is not moisture-dependent. Defects are thus identified irrespective of the extent to which the cigarette has dried out. With appropriate calibration, it is possible to measure the dry value of the area-related mass directly (if the moisture signal relating to a moisture measurement is used).
2. The moisture in the cigarette end can be measured in parallel.
3. The signals are very largely type-independent and independent of additives in the tobacco. They are also equipment-independent. Only a single basic calibration is therefore required before delivery of the equipment, and this can be transferred to other equipment with the same resonator type.
4. The signals are independent of color fluctuations in the tobacco.

Two methods may be used to assess the signal to determine whether a defect is present:

1. Once the equipment has been calibrated for the area-related mass $m_f$ using the relationship (4) a limit value $m_{fG}$ is defined. If this limit value is undershot during the on-line measurements, the relevant cigarette is characterized as being faulty.
2. The equipment is calibrated for measurement of the area-related mass $m_f$ using the relationship (4). During the measurement process, the sliding mean value of the area-related masses $m_{fMW}$ is formed over a large number of cigarettes. If the measured value of the area-related mass $m_f$ of an individual cigarette falls below this mean value to a greater extent than a limit value $\Delta m_{fMG}$ to be defined (quoted as a percentage of the sliding mean value), the relevant cigarette is characterized as being faulty. Thus, in this case, there is no need for any absolute value indication of the area-related mass, and all that is of interest is the signal relative to a sliding mean value of a large number of cigarettes. The equation (4) is therefore required only for moisture compensation.

Since, in the case of the microwave resonator method, the resonance characteristics of the empty microwave resonator are always compared with those of the resonator when loaded with measured goods, the resonance characteristics of the empty resonator must be measured from time to time (empty adjustment). The resonance characteristics of the empty resonator vary as a result of temperature fluctuations and as a result of possible dirt on the surface. There are various possible ways to carry out this empty adjustment:

1. The sensors are moved away from the measured goods at periodic time intervals by means of a suitable mechanical device. Once the sensors have been moved away from the measured goods, the empty adjustment is carried out, and the sensors are then moved back into contact with the measured goods.
2. In the case of measurements on the transport apparatus on which the cigarettes are arranged in groups, the empty measurement can be carried out automatically in unoccupied gaps on this transport apparatus. The empty measurement could thus be carried out during each revolution of the transport apparatus.
3. In the case of measurements on the transport, apparatus on which the cigarettes are arranged in groups, the empty measurement can be carried out in a specific area of the transport apparatus which is occupied by a blank plate, for example composed of plastic. The other signals relating to the influence of temperature and dirt can be corrected by periodic measurement of this blank plate.

It is particularly important to carry out the empty adjustment regularly when the measurements are evaluated using method 1 (determination of an absolute value). The empty measurement may be dispensed with entirely, or it must be carried out only on rare occasions, when using method 2 for evaluation (determination of the difference from the mean value).

There are various possible ways to install the microwave sensors in a cigarette packer. The options for segregation of the faulty cigarettes are associated with this installation:

1. Before being combined into groups, on a special transport apparatus, the cigarettes are supplied to this apparatus through an inlet funnel in a plurality of layers (see FIG. 8), with the cigarettes 1 being arranged one above the other in separate rows at the end of the funnel. Faulty cigarettes can be detected by placing microwave resonators 6 in these rows in the inlet funnel. In order to identify a cigarette 1 in its optimum position relative to the sensor 6, it is possible to make use of the fact that the area-related mass value passes briefly through a minimum between two cigarettes, and the measured value of interest appears as a relative maximum between two relative minima. This can also be associated with time scaling, coupled to the machine cycle rate, or with a light barrier for measured value recording, since the cigarettes 1 pass the sensor at approximately equal time intervals. Since the number of rows in the inlet funnel is equal to the number of cigarettes 1 per pack and one sensor 6 is required in each case for each row of cigarettes 1, the number of sensors 6 required is equal to the number of cigarettes 1 per pack (if the detection process is carried out at both ends of the cigarette, the number is twice as great). Once faulty cigarettes 1 have been detected, they can be segregated individually by means of an appropriate mechanical device. This is illustrated schematically in FIG. 8 where, by way of example, a device 16 is also schematically illustrated, by means of which faulty cigarettes 1 are ejected (this could also be done pneumatically by means of an air pulse).
2. The detection of faulty cigarettes can also be carried out after the cigarettes have been combined to form groups on the transport apparatus (see FIG. 9). An individual sensor 6 is required for each cigarette layer in these groups. The number of sensors required in this case is thus equal to the number of cigarette layers in the cigarette pack (if the detection process is carried out at both ends of the cigarette group-, the number is twice as great). When a faulty cigarette is detected in this case, the entire cigarette group is ejected on a group basis. The measured values can in this case be recorded at a time which the packaging machine defines as an electrical pulse, since the positions of each individual cigarette on the transport apparatus are linked to the machine clock cycle, and are defined in a fixed manner. This is shown schematically in FIG. 9. The cigarettes 1 are moved past sensors 6 in a holder 19 in groups in the direction of the arrow 18 by holders 17 for these cigarette groups. When the sensors 6 detect a faulty cigarette 1, the entire group is ejected by the unit 20.

Figure 8:
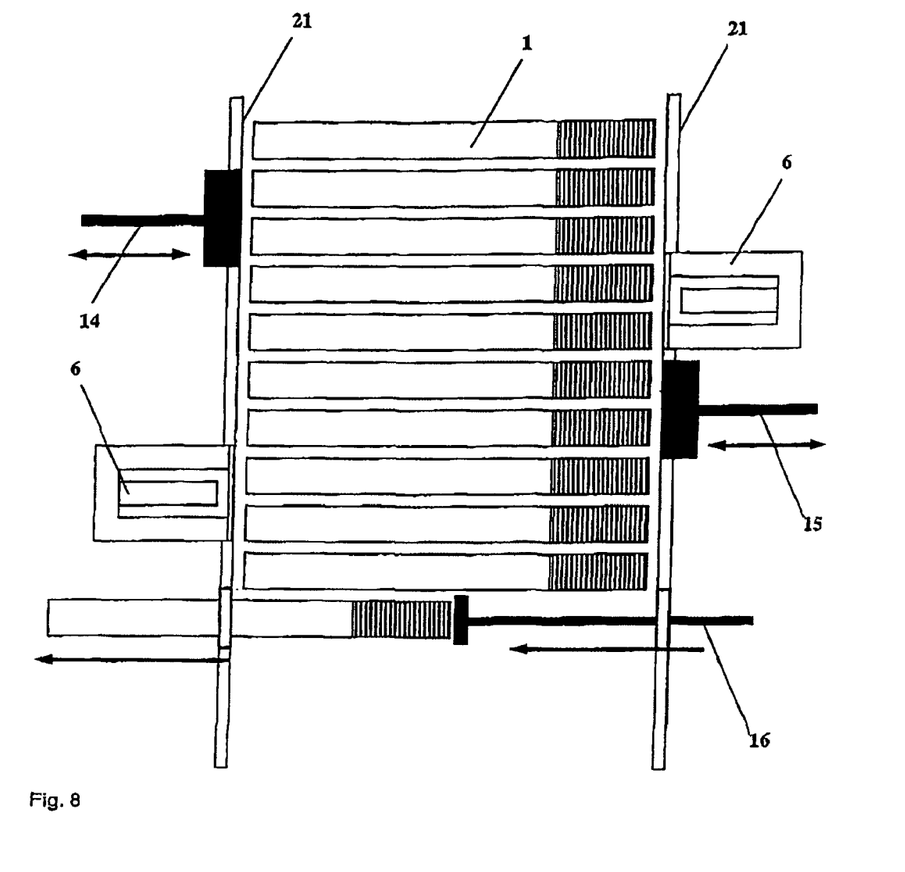
FIG. 8 shows an illustration of the apparatus for detection and segregation of individual cigarettes from the side.
Figure 9:
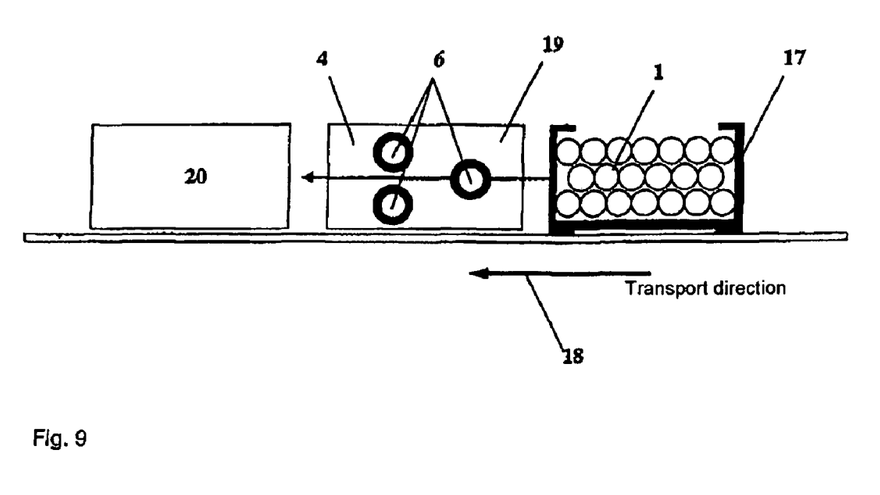
FIG. 9 shows another apparatus for detection and segregation of cigarette groups from the side.

Since the signals from the microwave stray field sensors 6 are dependent on the distance between the sensor 6 and the cigarette 1, a mechanical device 14, 15 is advantageous which aligns the cigarettes 1 directly in front of the sensors 6 by mechanical pressure against a plate 21 which is located at the same height as the microwave sensors 6. This ensures hat all of the cigarettes are located at the same distance from the microwave sensors during the measurement.

Figure 10:
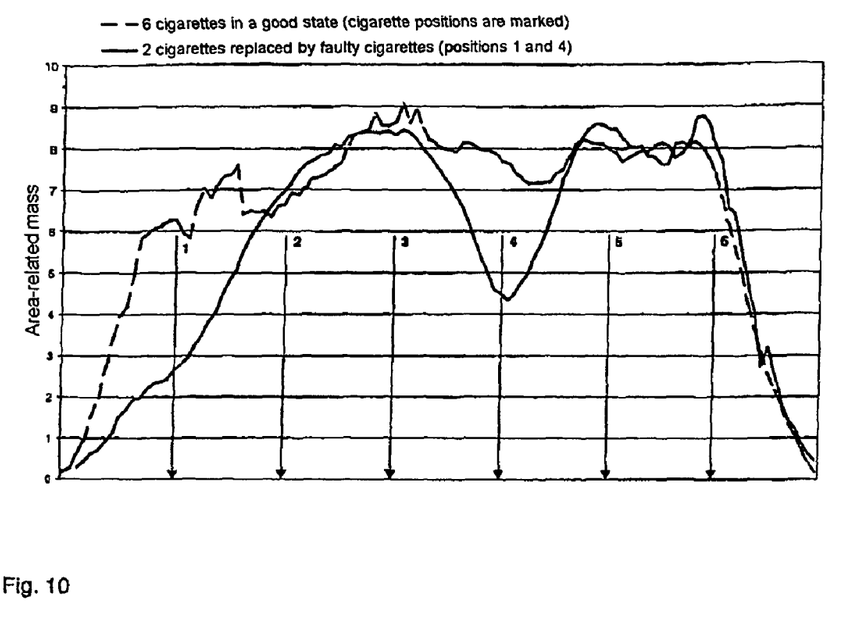
FIG. 10 shows an example of the profile of the area-related mass measurement.

By way of example, FIG. 10 shows the measurement of the moisture-compensated area-related mass (dimensionless in this case) for a row of six cigarettes whose positions are shown in the figure. The measurement was initially carried out with six intact cigarettes. The cigarettes at the positions 1 and 4 were then replaced by cigarettes with a defect (tobacco falling out of the head). The measurement curves illustrated in FIG. 10 show that the faulty cigarettes can clearly be detected by the microwave resonator measurement.

The invention claimed is:

1. An apparatus for detection and segregation of faulty cigarettes from a conveyed sequence of cigarettes, each cigarette having a generally cylindrical shape extending between opposite longitudinal ends, each longitudinal end having a cigarette end surface of a first diameter, said apparatus located in a production/packaging installation for cigarettes that includes an ejector which segregates faulty cigarettes from the conveyed sequence of cigarettes, said apparatus comprising:

a radio-frequency generator;
a sensor having a sensor end face and operatively connected to said radio-frequency generator so that a radio-frequency electromagnetic field having a second diameter is present adjacent said sensor end face, said second diameter being approximately same as said first diameter;
an evaluation circuit connected to detect and evaluate changes in said radio-frequency electromagnetic field;
said sensor end surface positioned so that the longitudinal end of each cigarette being evaluated passes through said radio-frequency electromagnetic field with the end surface generally parallel with the sensor end face and in a direction generally parallel with said sensor end face, said evaluation circuit detecting changes in said radio-frequency electromagnetic field corresponding to a faulty cigarette and providing a signal to the ejector to segregate the faulty cigarette from the conveyed sequence of cigarettes.

2. The apparatus as claimed in claim 1, wherein sensors are provided for both longitudinal ends of the cigarette.

3. The apparatus as claimed in claim 1, wherein the sensor has two conductor structures on said sensor end surface, which conductor structures have an electromagnetic stray field and are connected to a capacitance measurement device configured to make a capacitance measurement corresponding to changes in said electromagnetic stray field caused by cigarettes passing through said stray field.

4. The apparatus as claimed in claim 3, wherein the capacitance measurement device has an LC circuit, with the conductor structures forming the capacitor with the electromagnetic stray field.

5. The apparatus as claimed in claim 1, wherein the sensor is a microwave resonator which is open on said end face pointing towards the cigarette, said microwave resonator includes a closed end opposite said open end face and has an electrically conductive pin on a longitudinal axis of the microwave resonator, which pin is fitted to the closed end of the microwave resonator and has a length which corresponds approximately to one quarter or three quarters of a microwave wavelength of microwaves generated by said resonator.

6. The apparatus as claimed in claim 5, wherein the pin has a length which is approximately 1 to 20% less than the axial extent of the microwave resonator.

7. The apparatus as claimed in claim 5, wherein the pin has a length which is less by approximately 2 to 8% than the axial extent of the microwave resonator.

8. The apparatus as claimed in claim 5, wherein the microwave resonator widens outwards in a truncated-conical shape at the open end face, and wherein the pin tapers in a truncated-conical shape at this end of the microwave resonator.

9. The apparatus as claimed in claim 5, wherein a diameter of the pin is approximately 30 to 90% of an internal diameter of the microwave resonator.

10. The apparatus as claimed in claim 5, wherein a diameter of the pin is approximately 65 to 85% of an internal diameter of a microwave resonator.

11. The apparatus as claimed in claim 5, wherein a diameter of the pin is approximately 30 to 70% of an internal diameter of the microwave resonator.

12. The apparatus as claimed in claim 1, wherein the open end face in the sensor is closed by a dielectric.

13. The apparatus as claimed in claim 1, wherein the open end face in the sensor is closed by a ceramic disk.

14. The apparatus as claimed in claim 1, wherein said sensor comprises a plurality of microwave resonators each microwave resonator provided at a point at which the cigarettes are arranged in groups to form a plurality of layers, with one microwave resonator being provided for each layer.

15. The apparatus as claimed in claim 1, wherein said sensor comprises a plurality of microwave resonators and the microwave resonators are provided at a point past which the cigarettes are passed individually.

16. The apparatus as claimed in claim 5, wherein said microwave resonator defines a resonator cavity surrounding said pin and at least one of the resonator cavity and the pin is cylindrically symmetrical.

17. An apparatus for detection and segregation of faulty cigarettes from a conveyed sequence of cigarettes, each cigarette having a generally cylindrical shape with a longitudinal axis extending between opposite longitudinal ends, each longitudinal end having a cigarette end surface of a first diameter, said apparatus located in a production/packaging installation for cigarettes that includes an ejector which segregates faulty cigarettes from the conveyed sequence of cigarettes, said apparatus comprising:
  a coaxial microwave resonator defining a resonator cavity with a longitudinal axis, said resonator has a sensor end face and is operatively connected to a radio-frequency generator to generate a microwave field having a second diameter adjacent said sensor end face, said second diameter being approximately same as said first diameter, said sensor end face arranged so that the longitudinal end of cigarettes being evaluated pass through said microwave field with the cigarette end surface generally parallel with said sensor end face and in a direction generally parallel with said end face; and
  an evaluation circuit connected to detect and evaluate changes in said microwave field,
  wherein said microwave field is substantially homogeneous at least over said first diameter in two dimensions at right angles to the cigarette longitudinal axis and changes in said microwave field corresponding to a faulty cigarette result in segregation of the faulty cigarette from the conveyed sequence of cigarettes.

18. The apparatus as claimed in claim 17, wherein said end face pointing towards the cigarette is open, said microwave resonator includes a closed end opposite said open end face and has an electrically conductive pin on the longitudinal axis of the microwave resonator, which pin is fitted to the closed end of the microwave resonator and has a length which corresponds approximately to one quarter or three quarters of a microwave wavelength of microwaves generated by said resonator.

19. The apparatus as claimed in claim 17, wherein the pin has a length which is approximately 1 to 20% less than an axial extent of the microwave resonator.

20. The apparatus as claimed in claim 17, wherein a diameter of the pin is approximately 30 to 90% of an internal diameter of the microwave resonator.

21. The apparatus as claimed in claim 17, wherein the open end face in the sensor is closed by a dielectric.

* * * * *